United States Patent [19]
Zerbst et al.

[11] Patent Number: 4,850,994
[45] Date of Patent: Jul. 25, 1989

[54] HYPODERMIC SYRINGE

[75] Inventors: Ekkehard Zerbst; Tim Peters; Hans-Eberhard Koralewski, all of Berlin, Fed. Rep. of Germany

[73] Assignee: Physionic Gesellschaft für Medizin-und Systemtechnik GmbH, Fed. Rep. of Germany

[21] Appl. No.: 67,451

[22] Filed: Jun. 10, 1987

[30] Foreign Application Priority Data

| Oct. 11, 1985 [DE] | Fed. Rep. of Germany | 3536754 |
| Oct. 11, 1985 [DE] | Fed. Rep. of Germany | 3536755 |
| Oct. 11, 1985 [DE] | Fed. Rep. of Germany | 3536756 |
| Nov. 1, 1985 [DE] | Fed. Rep. of Germany | 3539247 |
| Mar. 18, 1986 [DE] | Fed. Rep. of Germany | 3609516 |

[51] Int. Cl.$^4$ ............................................. A61M 5/32
[52] U.S. Cl. ...................................... 604/198; 604/263
[58] Field of Search ................ 604/192, 197, 198, 263

[56] References Cited

U.S. PATENT DOCUMENTS

| 2,571,653 | 10/1951 | Bastien | 604/198 |
| 4,356,822 | 11/1982 | Winstead-Hall | 604/117 |
| 4,631,057 | 12/1986 | Mitchell | 604/198 |
| 4,681,567 | 7/1987 | Masters et al. | 604/198 |

Primary Examiner—Martin P. Schwadron
Assistant Examiner—Allen J. Flanigan
Attorney, Agent, or Firm—McGlew & Tuttle

[57] ABSTRACT

The invention relates to a hypodermic syringe in which a hollow needle is surrounded by a protective sheathing in such a way that after the injection has been performed the protective sheathing encloses the tip of the hollow needle to provide protection.

5 Claims, 7 Drawing Sheets

FIG. 1
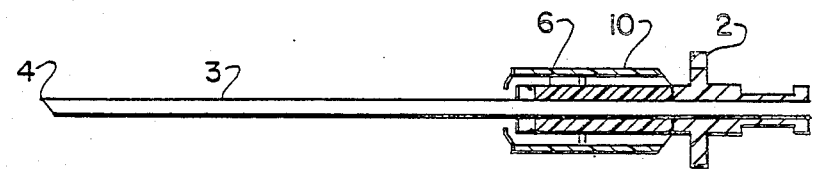
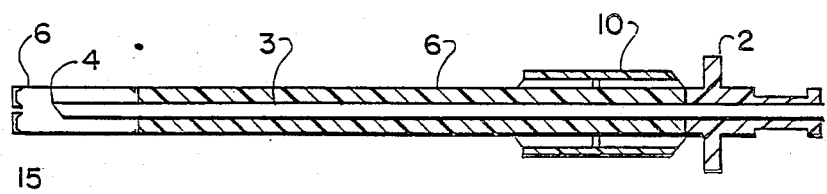
FIG. 2
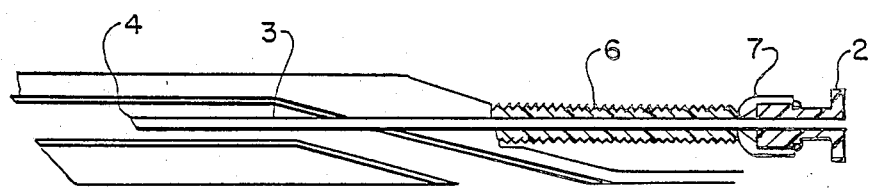
FIG. 3

HYPODERMIC SYRINGE

BACKGROUND OF THE INVENTION

Field of the Invention

This invention relates, in general, to the construction of needles and similar instruments which are designed to enter a person's skin and to an improved needle and hypodermic syringe construction having a retractable protective sheathing protecting a catheter-ejecting needle.

This invention relates to a hypodermic syringe that can be designed as a disposable, multi-use or special-purpose syringe. Such hypodermic syringes can be used to take blood or other fluids from a subject or to inject medications or the like into a subject.

The particular nature of newly discovered infectious diseases which have no known cure or are difficult to treat, such as AIDS, where infection may be transferred via blood, bodily secretions or portions of tissue from the patient to others, including the treating physician or medical aids or nursing staff, makes procedures with medical instruments, particularly with hypodermic syringes, very dangerous with such patients. This focus of hazard is also present when substances dangerous in themselves are to be applied by means of a hypodermic syringe or needle. This is always the case when procedures are carried out in laboratories or in industry with substances dangerous to health or otherwise hazardous, such as radioactive materials.

SUMMARY OF THE INVENTION

The invention provides a hypodermic syringe that offers optimal protection.

Accordingly, the invention provides a skin-penetrating needle construction which includes a protective sheathing over a needle which extends beyond the tip and protects the needle, but which will be automatically retracted upon the insertion of a needle into the person's skin.

A further object of the invention is to provide a hypodermic syringe which includes a syringe cylinder having needle assembly connected thereto for the passage of a fluid through the needle from the cylinder which includes a protective sheathing overlying the needle which extends beyond a penetrating tip thereof which has an opening which is made of a construction such that it will be moved backwardly upon insertion of the needle into the skin to uncover the needle for the penetration through the skin.

A further object of the invention is to provide a protective device for injecting needles which are simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

The invention provides for a protective sheathing for hypodermic syringes that can be so formed and produced in each case that it can be attached either in advance or subsequently to the usual commercially available syringes of various types and sizes. Suitable materials for this protective sheathing may be plastics, glass and/or metals.

In an advantageous and simple embodiment, the protective sheathing is a flexible tube, particularly one made of plastic, slidable over the hollow needle and either attached at the time the hypodermic syringe is manufactured or supplied separately as a modular component and mounted when needed. It is particularly advantageous if the flexible tube can be compressed like a bellows or comes already compressed like a bellows.

The flexible tube may be drawn over the hollow needle prior to use of the syringe and held by means of an attachment piece on the needle joining piece. When the needle is used, is applied to the injection site and penetrates the tissue or the blood vessel, the protective tube of an elastic material compresses in bellows fashion. When the injection is completed and the hollow needle is drawn out of the blood vessel and tissue, the protective tube, thanks to its own elasticity, can again stretch out so that it protectively encases the tip area of the hollow needle. The user, however, could also, when drawing the hollow needle out of the injection site, set his finger on the compressed protective sheathing and push it in the direction of the needle tip, so that once the needle has been completely withdrawn from the tissue, the needle tip is covered.

In a particularly advantageous version, the protective sheathing can have an abutment that lies in front of the tip of the hollow needle when the sheathing is in extended position. The abutment is attached to the inner wall of the protective sheather or protective flexible hose. Prior to the injection procedure, the tip of the needle can be allowed to project through by means of a slight angling of the sheathing. After the injection procedure, this abutment prevents the needle tip from re-emerging out of the protective sheathing.

The protective sheathing can also be a segment of a rigid tube axially slidable on the hollow needle. It may be, for example, a segment of metal or glass tubing that can be slipped onto the hollow needle prior to the injection by means of an interposed axial pressure spring.

In another embodiment, the protective flexible tube can be mounted on the needle joining piece in compressed, bellows-like state with the aid of a releasable retainer. In such an embodiment, the protective flexible tube may be mounted in advance on the hypodermic syringe or may be mounted just before use. Upon uncoupling or release, the flexible tube compressed like a bellows is able to slide along the hollow needle by virtue of its own inherent elasticity. The flexible tube compressed like a bellows can also be shifted by the effects of a gas under pressure, or the compressed flexible tube may be acted upon by a pressure spring surrounding the hollow needle.

Prior to and during the injection procedure, the protective flexible tube is folded back on itself and is held in that folded condition on the needle joining piece by a retaining device until the injection process or the process of taking blood or fluid or other material is completed, whereupon the retaining device is released by the pressure of a finger. The releasable retainer can be a spreadable spring sleeve with spreadable spring jaws.

The protective flexible tube can also be double-walled and closed on one side. A pressurized gas container can be built in which expands the folded flexible tube when the pressurized gas container is ruptured or opened by the press of a finger, causing it to slide forward over the hollow needle.

The propulsion spring or propulsion device for the protective flexible tube may be permanently built into the needle mount for multiple use. In this arrangement, on each occasion the protective flexible tube, folded like an accordion, is pushed back over the hollow needle and firmly attached to the needle mount. To propel the protective flexible tube forward, a propulsion spring built into the needle mount and compressed is released by freeing a retaining device by means of finger pressure.

In particular, the tip of the protective flexible tube can be so designed on its inner side that after the flexible tube slides past the tip of the needle flexible constrictions and/or flexible closure elements on the protective flexible tube swing out in such a way as to prevent the needle tip from sliding out again from the opening of the tube.

It also falls within the purview of the invention to design the syringe cylinder and the hollow needle to be axially slidable relative to one another so that after the injection, by a relative motion of the two parts, the syringe cylinder encompasses the tip area of the hollow needle, acting as protective sheathing. In a particularly advantageous version, the hollow needle and/or the needle assembly can be so designed that it is slidably mounted in the syringe cylinder. The end of the hollow needle or needle assembly positioned inside the syringe cylinder may be couplable with the syringe plunger.

If the hollow needle is seated in the front portion of the syringe cylinder in such a way that it is sealed but can move along with the needle mount, then, for example, after completion of the injection procedure by coupling with the syringe plunger by means of conventional connecting elements as the syringe plunger is drawn back a relative movement is induced that draws the hollow needle back into the syringe cylinder, so that the latter surrounds the hollow needle, acting as a protective sheathing.

Low pressure or a partial vacuum is one means of effecting the coupling. A locking device can be provided for the channel of the hollow needle by means of which the syringe is hermetically sealed following completion of an injection. As the plunger is drawn back, a vacuum is created between the needle mount and the plunger, so that the needle mount can be drawn backward along with the plunger. A particularly advantageous feature is to have a catching lug on the needle mount engage in a catch groove in the syringe cylinder at the end of the withdrawal stroke to provide a greater degree of safety.

In another embodiment, the syringe cylinder is sheathed by a protective cylinder. In this arrangement, the syringe cylinder is held before and/or during the injection or during the aspiration of blood, bodily fluids or other laboratory fluids by a flexible back stop on the protective cylinder. After completion of the injection or completion of the aspiration process, a forcible pull on the syringe plunger bringing it back to the rear wall of the syringe cylinder can overcome the force of the back stop. The syringe cylinder then emerges from the protective cylinder. In the process, the hollow needle is drawn through the front opening in the protective cylinder into its interior. The hollow needle may be switched by means of a needle joining piece on the syringe cylinder. On the opening in the protective cylinder on the needle side, devices may be located that close tight against fluid passage after the syringe cylinder is drawn out of the protective cylinder. It can be arranged that solutions may be applied after the hollow needle is pulled in in order to sterilize and/or neutralize harmful substances.

The protective cylinder may have a catch lug that engages in the syringe cylinder and projects into the path of the stroke of the plunger. When the plunger is pulled back, this lug catch is released, allowing for relative movement between the syringe cylinder and the protective cylinder. In this arrangement the syringe cylinder may have other catch points for the catch lug on the protective cylinder, particularly on its front end.

A protective cylinder can also be mounted to slide axially on the syringe cylinder of a pre-produced hypodermic syringe and after the injection be moved into a position in which it covers the tip of the hollow needle. Such a protective cylinder is manufactured and delivered separately from the syringe itself. Said protective cylinder may have a catch that holds it in mounted position on the syringe cylinder. On the end the protective cylinder may have a locking means that locks the protective cylinder in extended protective position following the injection. This practically rules out the danger of injury. In a simple embodiment, the locking means may be a locking ring mountable along with the protective cylinder on the syringe cylinder.

The protective sheather on the syringe cylinder may take the form of two half-shells constituting a protective cylinder cut in half lengthwise which are seated in channels on the syringe cylinder. These semi-cylindrical shells can be pivoted out of this position by means of joints with the aid of tilting springs on the needle end of the syringe cylinder 180° into a position in which the hollow needle, including its tip, is covered. The channels so be so designed that the half-shells of the protective sheathing are seated so that the syringe can be handled without touching the edges of the half-shells in their resting position.

It is also possible to design the protective sheathing so that two half-shells are seated to be axially slidable on the syringe cylinder. Said half-shells may be held together by spring washers or joined to one another by means of spring elements.

The protective sheathing may also consist of two protective strips capable of pivoting 180° with the aid of tilt springs, said strips being seated on the syringe cylinder in such a way that they can be pivoted from a position in which they flank the syringe cylinder into a position in which they cover the hollow needle, providing protective sheathing.

This type of protective sheathing may be positioned either on the needle assembly or on the cylinder.

It is also possible to design the protective sheathing as a screen with a flexible, but perforation-proof covering, the screen being swung 180° from its closed rest position to an open position in which it covers the needle tip.

The protective needle sheathing, which takes the form of a casing, can be provided with a handle so that when the protective casing is handled the hands can be kept a safe distance from the sharp point of the needle.

The protective casing or sheathing of the hollow needle may have an asymmetrically placed opening or spot prepared for perforation, next to which a pad is provided. Prior to use, the sheathing or protective casing is pressed back and the needle tip emerges from the opening. After use, the protective casing is extended. The pad on the end thereby comes to rest in front of the tip of the needle. By a light reverse spring action, the needle tip is made to penetrate the cushion and is thereby secured against further perforation. This pad closure offers extra protection against the escape of fluids.

Embodiments of the invention will be explained in the following description with reference to the drawing figures.

BRIEF DESCRIPTION OF THE DRAWINGS

They show:

FIGS. 1-5 are sectional views of embodiments in which the protective sheathing is a flexible tube capable of compression and extension like a bellows;

FIG. 1 shows a section of a hollow needle 3 with its needle joining piece 2. As FIG. 2 shows, after the injection, the hollow needle 3 is encased by a protective flexible tube 6 in such a way that its tip 4 is completely covered.

Figure 4:
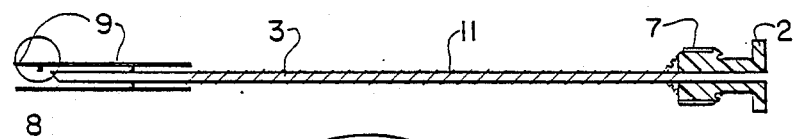

In the depiction in FIG. 1, the protective flexible tube 6 is compressed bellows-fashion and is held in this compressed state by a releasable retainer 10. After the injection, pressure may be exercised on this retainer 10 to release the protective flexible tube 6. If the protective flexible tube 6 is made of an elastic, resilient material, the protective flexible tube 6 will return itself to the position depicted in FIG. 2 once the retainer 10 is opened. At the front end 15 of the flexible tube 6 additional closing elements are provided that close around the tip 4 and guarantee secure seclusion of the tip 4.

It is also possible to provide a pressure spring to push out the protective flexible tube 6.

The retainer 10 may be a spreading spring sleeve, whose spreading arms are pressed apart by pressing on the back end of the spring sleeve.

It is also possible to design the protective tube 6 as a double-walled, sack-like tube that admits gas under pressure; the pressurized gas admission can be actuated by the press of a finger.

In the embodiment shown in FIG. 3, the protective flexible tube 6 is mounted on the hollow needle 3 subsequent to production, i.e., just before use of the hypodermic syringe.

The protective flexible tube 6 has an attaching end piece 7. By means of this attaching end piece 7, the protective flexible tube 6 is locked onto the needle joining piece 2.

As shown in FIG. 3, as the injection is performed, the protective flexible tube 6 compresses like a bellows, and when the hollow needle 3 is drawn out, said flexible tube 6 can again expand over the tip 4 of the hollow needle 3. If, however, the material's elasticity is somewhat less, it is possible for the user to slide the protective flexible tube 6 forward with the fingers into protective position.

As shown in FIG. 4, the protective sheathing may also take the form of a segment of a rigid tube 9. Said rigid tube 9 may be a piece of glass tubing, metal tubing or rigid plastic tubing. By means of a spring 11 the rigid tubing segment 9 can be pushed into protective position.

Figure 5:
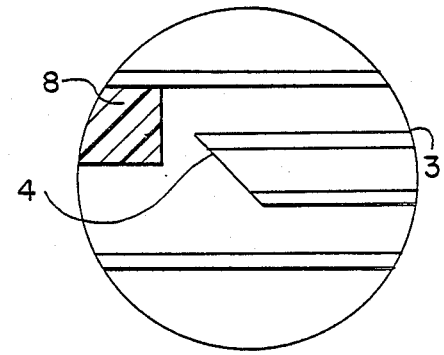

As shown in FIG. 5, inside the protective sheathing an abutment 8 is provided facing inward, so positioned that said abutment 8 comes to rest ahead of the tip 4 of the hollow needle 3 when the protective sheathing is in extended position. From here, with a downward bend the tip 4 can be pushed past the abutment 8. After the injection, this abutment 8 prevents the tip 4 from emerging out of the protective sheathing.

Figure 6:
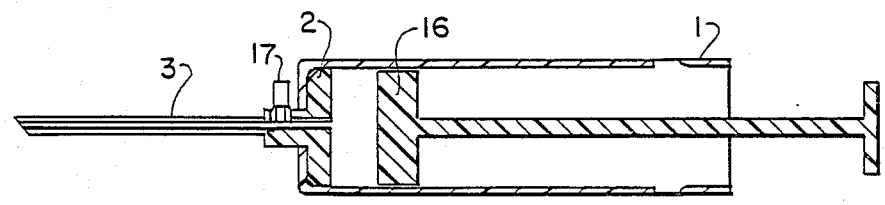
FIGS. 6-17 are schematic sectional view depictions of further embodiments in which the protective sheathing is composed of cylinder elements.
Figure 7:
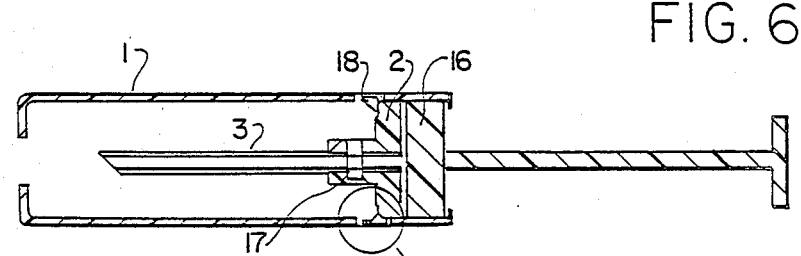
Figure 8:
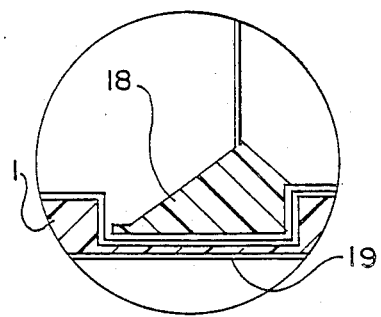

In the embodiment shown in FIGS. 6-8 the hollow needle 3 can move along with the needle joining piece 2, but it is seated in a sealed arrangement in the front portion of the syringe cylinder 1. After completion of the injection procedure, the syringe plunger 16 becomes coupled to the needle joining piece 2. Conventional means may be used to accomplish this coupling, such as a tongue-and-groove connection, a catch connection or a bayonet lock connection.

In the embodiment depicted, a locking device 17 is positioned in the needle joining piece 2. When, after an injection has been performed, the syringe plunger 16 lies against the needle joining piece 2, the locking device 17 is closed. If the syringe plunger 16 is then pulled back, because of the diminished pressure created between the syringe plunger 16 and the needle joining piece 2, the syringe plunger 16 carries the needle joining piece 2 back with it, so that, as FIG. 7 shows, the hollow needle 3 is completely surrounded by the syringe cylinder 1, which in this instance assumes the function of the protective sheathing.

As shown in FIGS. 7 and 8, a locking arrangement is provided at the end position of the hollow needle 3 in the syringe cylinder 1 for reasons of safety. On the needle joining piece 2 is positioned a catch device 18, which may consist, for example, of an elastic ring. When the needle joining piece 2 is drawn back, said elastic catch device 18 can be caught in a catch groove 19 built into the syringe cylinder 1, so that the hollow needle 3 can be held securely in its protected position.

Figure 9:
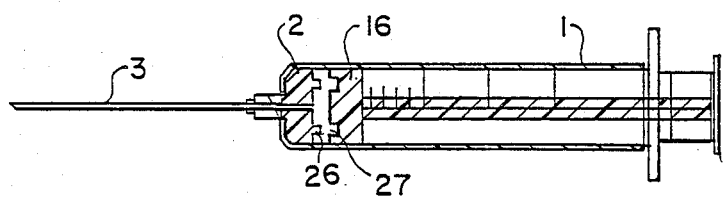
Figure 10:
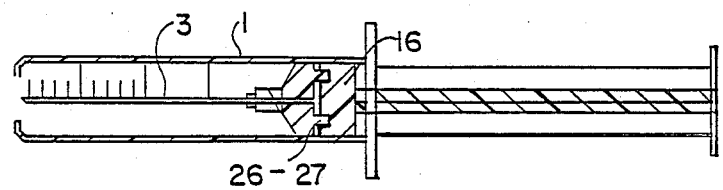

FIGS. 9 and 10 depict schematically coupling elements 26 and 27 that can be positioned on or built into the needle joining piece 2 and the syringe plunger 16. Coupling elements 26 and 27 are in themselves conventional coupling elements that can be caused to engage with one another by means of an axial motion, a rotational motion or a combination of the two motions so that the needle joining piece 2 after coupling is necessarily moved from the position shown in FIG. 9 to the position shown in FIG. 10. With this embodiment, as well, a locking arrangement can be provided for the needle joining piece 2 in its end position.

Figure 11:
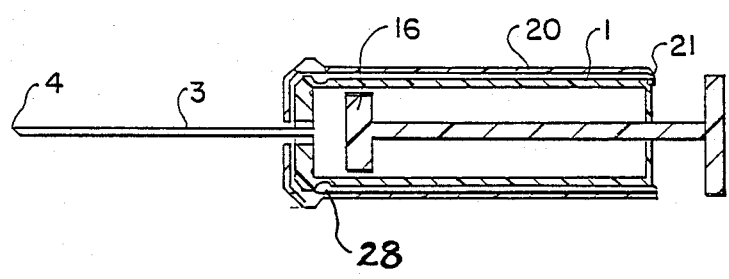
Figure 12:
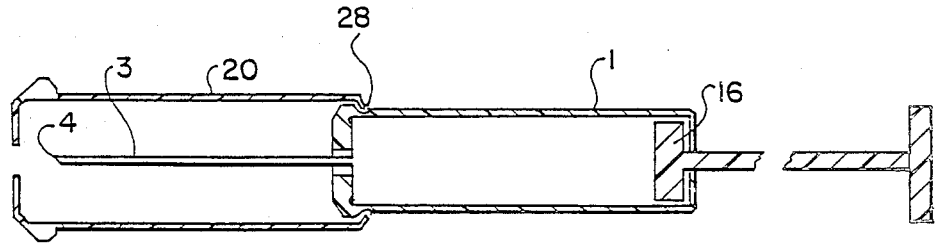

FIGS. 11 and 12 illustrate an embodiment in which the syringe cylinder 1 is sheathed in a protective cylinder 20. Said protective cylinder 20 may be made of metal, glass or plastic.

The protective cylinder 20 may be supplied along with the hypodermic syringe, that is, already mounted on it. It could also, however, be mounted later, e.g., shortly before the injection. Said protective cylinder 20 surrounds the syringe cylinder 1 before and/or during the injection, or during the taking of blood or some other bodily or laboratory fluid. The protective cylinder 20 grasps the back end of the syringe cylinder 1 by means of an elastic back stop 21. This back stop 21 maintains a firm grip until after completion of the injection or completion of the aspiration process the holding power of the said elastic back stop 21 is overcome by a forcible pull backward on the syringe plunger 16. The hollow needle 3 is thereby brought into the protected position shown in FIG. 12 in which the tip 4 of the hollow needle 3 is located inside the protective cylinder 20. In this position, the protective cylinder 20 can catch at point 28, so that it is secured.

Figure 13:
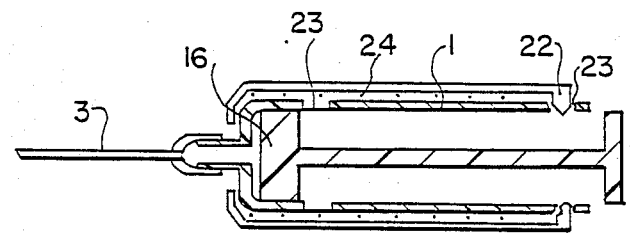
Figure 14:
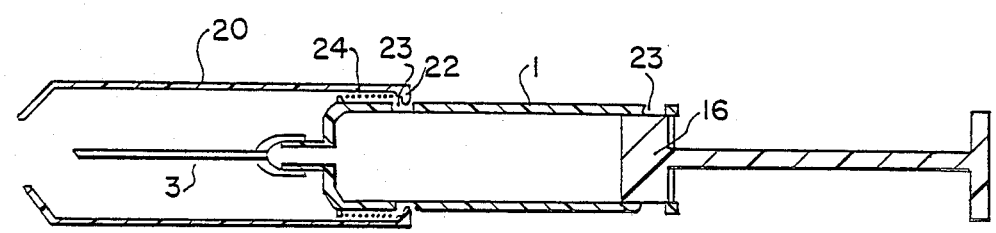

In the embodiment shown in FIGS. 13 and 14, the protective cylinder 20 has a catching lug 22. Said catching lug 22 passes through a groove 23 in the syringe cylinder 1 and extends into the path of the stroke of the syringe plunger 16.

If, for example, a fluid sample is taken with this syringe, upon reaching the position shown in FIG. 14 the syringe cylinder 16 can force the catching lugs 22 out of the groove 23, thus releasing the catch connection between the syringe cylinder 1 and the protective cylinder 20, so that the protective cylinder 20 can be moved to the position shown in FIG. 14. A tension spring 24, shown in FIG. 13 under tension, between the syringe cylinder 1 and the protective cylinder 20 can automatically move the protective cylinder 20 into the position shown in FIG. 14.

As shown in FIGS. 13 and 14, additional grooves 23 can be provided in the syringe cylinder 1 to bring about secure locking after withdrawal of the hollow needle 3.

Figure 15:
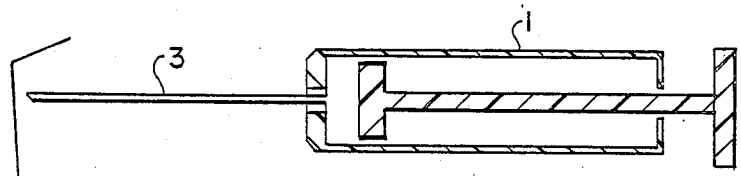
Figure 15:
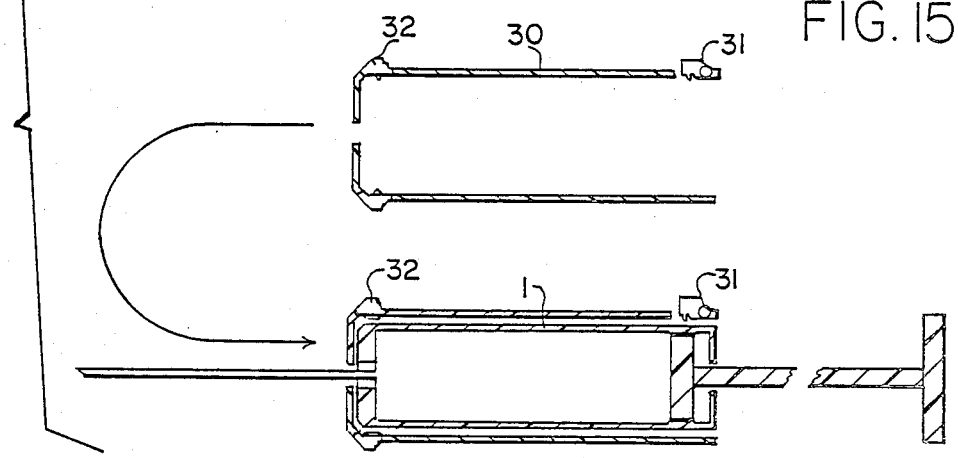
Figure 16:
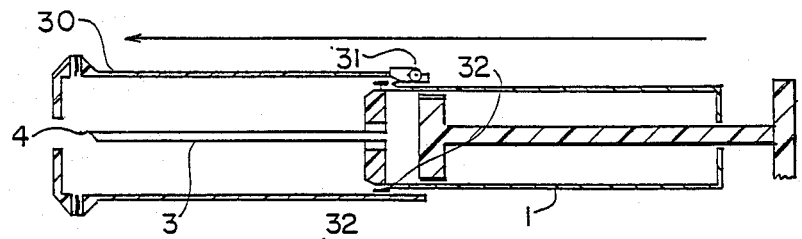
Figure 17:
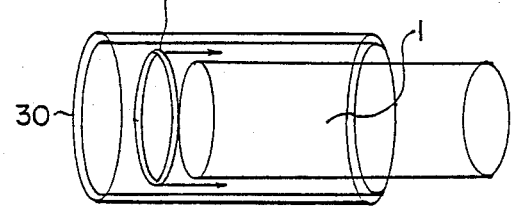

FIGS. 15–17 illustrate an embodiment in which the extra, protective cylinder 30 shown in FIG. 15 can be mounted later on the syringe cylinder 1 shown in FIG. 15 by sliding. The protective cylinder 30 has a ring-shaped locking means 32 on the front end and a latching means 31 on the back end, in the form of a hook in the particular embodiment illustrated.

In the operating position shown in FIG. 15, the syringe is ready for use; after the injection, the ring-shaped locking means 32 can be released and the syringe cylinder 1 can be withdrawn as shown in FIG. 16 out of the protective cylinder 30. In end position, the latching means 31 catches in the locking means 32, so that the end position of the tip 4 of the hollow needle 3 is secured.

The material from which the protective cylinder 30 shown in FIG. 17 is made may have the elastic and plastic qualities of known plastics. The sheathing of the hollow needle 3 may be accomplished by the user, as he withdraws the hollow needle 3 from the injection site, placing a finger on the protective cylinder 30 and thus shifting it in the direction of the tip 4, so that once the hollow needle 3 is fully withdrawn, its tip 4 is covered.

Figure 18:
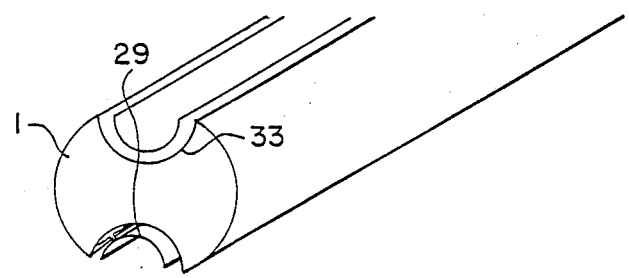
FIGS. 18-21 Examples of other special embodiments of protective sheathing systems.
Figure 19:
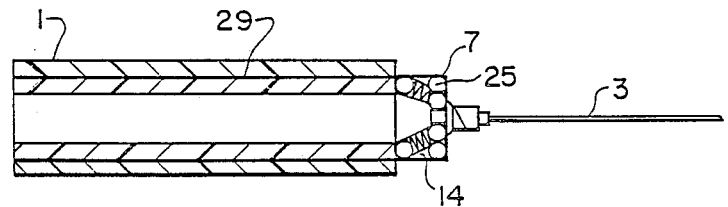

In the embodiment shown in FIGS. 18 and 19, channels 33 are cut into the syringe cylinder 1. In these channels are seated semi-cylindrical shells 29. Said semi-cylindrical shells 29 are pivotally mounted at point 25, on the attaching endpiece 7, for example, and are acted upon by tilting springs 14. When swung 180° around the rotation point 25, these semi-cylindrical shells form a protective sheathing surrounding the hollow needle 3. The semi-cylindrical shells 29 are mounted in the channels 33 in such a way that with normal handling of the syringe the edges of the said semi-cylindrical shells 29 is not affected.

Figure 20:
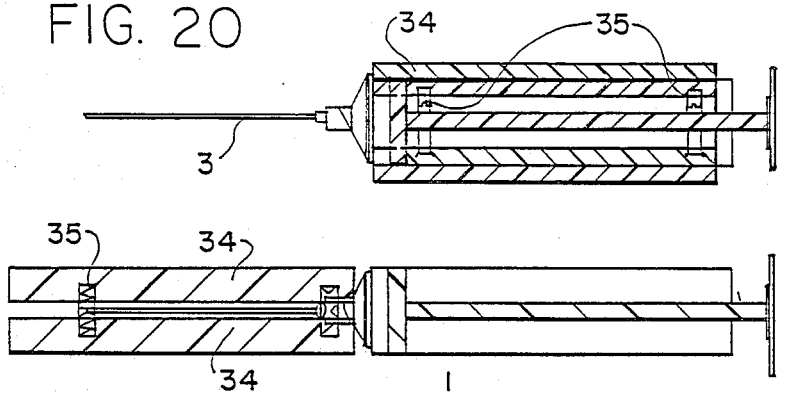
Figure 21:
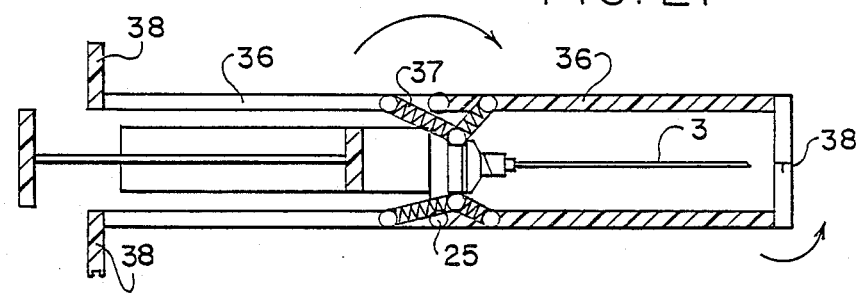

In the embodiment shown in FIGS. 20 and 21, the protective sheathing is formed by two semi-cylindrical shells 34, which slide axially along the syringe cylinder 1. Said semi-cylindrical shells 34 may be held together by spring washers tensioned around their circumference.

It is also possible, however, to provide holding springs, as shown at point 35, so that as the semi-cylindrical shells 34 are moved forward into the position shown in FIG. 21, the semi-cylindrical shells are drawn together to form a protective sheathing for the hollow needle 3.

Figure 22:
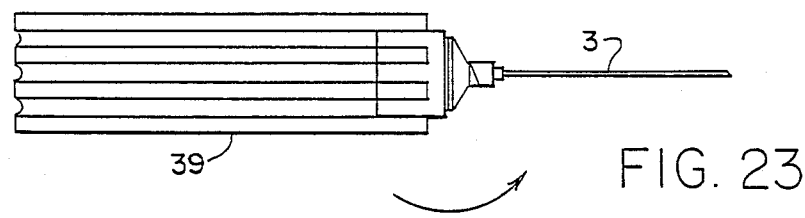
FIGS. 22-26 are sectional and one perspective view (FIG. 17) of special designs for the protective tube.

FIG. 22 shows a syringe cylinder which has two protective strips 36 pivotally mounted around the rotation point 25 and acted upon by tilting springs 37. Said protective strips 36 may have catch devices 38 on the end. In pivoted position, these protective strips surround the hollow needle 3 in a type of open protective sheathing, the catch devices 38 snapping together to close the protective sheathing in front.

Figure 23:
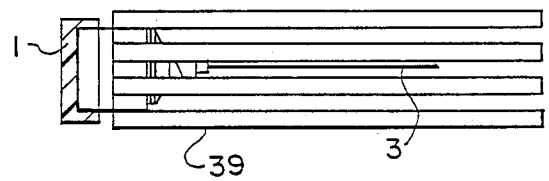
Figure 24:
Figure 25:
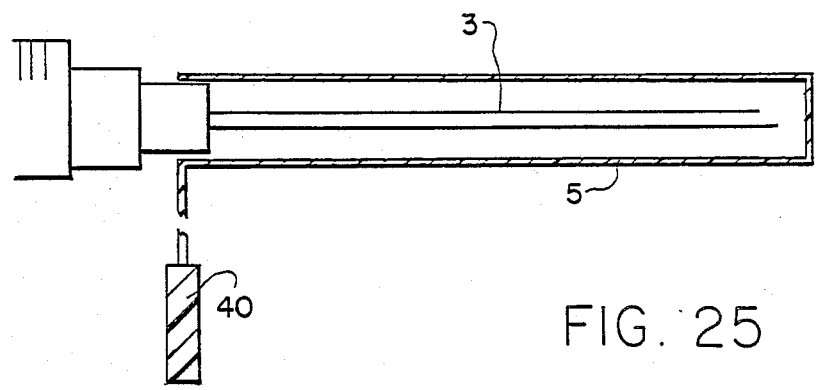

FIGS. 23 and 24 show an embodiment in which the protective sheathing is designed as a screen 39. Said screen 39 has a covering that is flexible but proof against perforation. Starting from the rest position shown in FIG. 23, the screen 39 can be rotated to 180° and assume the position schematically illustrated in FIG. 24, in which the said screen surrounds the tip of the hollow needle 3.

As shown schematically in FIG. 24, the protective needle covers 5 described can be so designed that they can be connected or equipped with an operating handle 40. With the said operating handle 40, when handling the protective needle cover 5, one can grip it at a safe distance from the sharp tip of the hollow needle 3.

Figure 26:
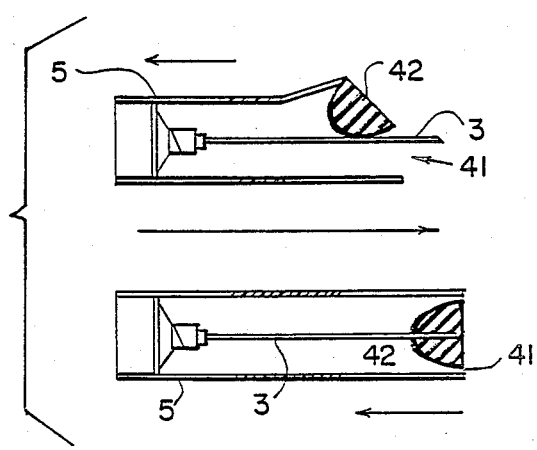

FIG. 26 shows two operating phases of yet another embodiment of a protective needle cover 5. This protective needle cover 5 can have a segment that is capable of expanding and contracting on the principle of a bellows and can have high inherent elasticity. This protective needle cover 5 has an asymmetrically positioned opening 41 or at that same spot a surface prepared for perforation. Next to the opening 41 or next to the prepared surface a pad 42 is provided. On delivery, the protective needle cover 5 can be angled in such a way that the sharp tip 4 of the hollow needle 3 lies opposite a perforation-proof portion of the cover.

While specific embodiments of the invention have been shown and described in detail to illustrate the application of the principles of the invention, it will be understood that the invention maybe embodied otherwise without departing from such principles.

Prior to use of the hollow needle 3, the protective needle cover 5 is first compressed, and the tip of the needle emerges from the opening 41. After use, the protective needle cover 5 is stretched out and the pad 42 is brought into position over the tip as shown in the bottom portion of FIG. 26. Because of the inherent elasticity, the needle tip then penetrates the pad 42. A perforation-proof closing is thus achieved. Said pad closing provides extra security against the escape of fluids.

We claim:

1. Hypodermic syringe characterized by a syringe cylinder, said syringe cylinder defining a liquid reservoir, a needle assembly (2,3) including a hollow needle having a first end in communication with said cylinder reservoir and having an opposite end with a tip (4), said needle assembly including a syringe plunger movable in said syringe cylinder (1), a protective sheathing (20) axially movable relative to said hollow needle (3), said sheathing being movable subsequent to withdrawal of the hollow needle (3) out of the injection site into a position in which the tip (4) of the hollow needle (3) is covered, said protective sheathing being designed as a protective cylinder (2) slidably mounted on said syringe cylinder (1), said syringe cylinder having a back rim, said protective cylinder (20) having an elastic flange acting as a back stop (21) that encircles said back rim of the syringe cylinder (1).

2. Hypodermic syringe characterized by a syringe cylinder, said syringe cylinder defining a liquid reservoir, a needle assembly (2,3) including a hollow needle having a first end in communication with said cylinder reservoir and having an opposite end with a tip (4), said needle assembly including a syringe plunger movable in said syringe cylinder (1), a protective sheathing (20) axially movable relative to said hollow needle (3), of the hollow needle (3) out of the injection site into a position in which the tip (4) of the hollow needle (3) is covered, said protective sheathing being designed as a protective cylinder (2) slidably mounted on said syringe cylinder (1), said protective cylinder (20) having a catching lug (22), said catching lug engaging in at least one spot with said syringe cylinder (1) and extending into the path of said syringe plunger (16).

3. Hypodermic syringe pursuant to claim 2 characterized in that:
   the protective cylinder (30) has a locking means (32) that holds the former on the syringe cylinder (1) in mounted position.

4. Hypodermic syringe pursuant to claim 2 characterized in that:
   the protective cylinder (3) has a latching means 31 on the end that holds the former after the injection in the drawn-out protective position (FIG. 16).

5. Hypodermic syringe pursuant to claim 2 characterized in that:
   the locking means (32) is a locking ring mountable along with the protective cylinder (30).

* * * * *